US006981590B1

United States Patent
Ubel et al.

(10) Patent No.: US 6,981,590 B1
(45) Date of Patent: Jan. 3, 2006

(54) APPARATUS AND METHODS FOR PACKAGING AND STORING MOISTURE-SENSITIVE PRODUCTS IN RESEALABLE POUCHES

(75) Inventors: F. Andrew Ubel, St. Paul, MN (US); Kurt Allenberg, Woodbury, MN (US); Charles C. Polta, St. Paul, MN (US); Anthony J. Campagna, Roseville, MN (US); Melvin Y. Wong, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 210 days.

(21) Appl. No.: 09/551,706

(22) Filed: Apr. 18, 2000

(51) Int. Cl.
*A61B 17/06* (2006.01)

(52) U.S. Cl. .................................. 206/440; 206/494
(58) Field of Classification Search ................ 206/440, 206/438, 205, 494; 383/9, 68, 61
See application file for complete search history.

(56) References Cited

U.S. PATENT DOCUMENTS

| | | | |
|---|---|---|---|
| 2,834,459 A | * 5/1958 | Rickard et al. ............ 206/440 |
| 3,629,905 A | * 12/1971 | Cote ........................ 24/30.5 R |
| 4,002,264 A | * 1/1977 | Marchesani ................ 221/63 |
| 4,609,578 A | 9/1986 | Reed |
| 4,667,661 A | 5/1987 | Scholz et al. |
| 4,703,518 A | * 10/1987 | Ausnit ........................ 383/63 |
| 4,770,299 A | 9/1988 | Parker |
| 4,774,937 A | 10/1988 | Scholz et al. |
| 4,869,046 A | 9/1989 | Parker |
| 4,899,738 A | 2/1990 | Parker |
| 5,003,970 A | 4/1991 | Parker et al. |
| 5,027,803 A | 7/1991 | Scholz et al. |
| 5,076,424 A | * 12/1991 | Nakamura ................ 206/205 |
| 5,505,305 A | 4/1996 | Scholz et al. |
| 5,582,853 A | * 12/1996 | Marnocha et al. .......... 426/122 |
| 5,622,431 A | * 4/1997 | Simonsen .................... 383/63 |
| 5,704,480 A | * 1/1998 | Scholz et al. ............... 206/438 |
| 5,003,970 A | 7/1999 | Parker et al. |
| 6,027,465 A | 2/2000 | Scholz et al. |

FOREIGN PATENT DOCUMENTS

| | | |
|---|---|---|
| BE | B65D | 11/1955 |
| BE | 542 694 | 11/1955 |
| CH | 265688 | 3/1950 |
| GB | 971552 | 9/1994 |
| WO | WO 95/19754 | 7/1995 |
| WO | WO 96/20884 | 7/1996 |

OTHER PUBLICATIONS

"Cellacast®–Longuette," German Language Product Brochure, Lohmann & Rauscher GmbH & Co., printed in Germany, 3 pages, (date unknown).
Pictures of Lohmann Cellacast™(labeled Figures A–D), 2 pages, (date unknown).

* cited by examiner

*Primary Examiner*—Luan K. Bui
(74) *Attorney, Agent, or Firm*—Daniel R. Pastirik; Matthew W. Adams

(57) ABSTRACT

The present invention relates to apparatus and methods for storing moisture-sensitive products such as moisture-curable orthopedic splinting/casting product, in flexible, preferably elongated, pouches. The product is folded into a repeating series of discrete sections where each section has at least one segment that extend along the pouch length. By configuring the product in this way, it can be efficiently packaged, stored, and dispensed. Other embodiments of the invention include closure systems that permit sealing the pouch opening when product is not being dispensed and substantially sealing the pouch around the product during dispensing.

27 Claims, 9 Drawing Sheets

APPARATUS AND METHODS FOR PACKAGING AND STORING MOISTURE-SENSITIVE PRODUCTS IN RESEALABLE POUCHES

TECHNICAL FIELD

This invention relates to moisture-sensitive products and, more particularly, to apparatus and methods for packaging and storing continuous length, moisture-curable orthopedic splinting/casting product in moisture-proof pouches and containers.

BACKGROUND

The orthopedic immobilization industry has developed a need for a resealable package used with continuous length moisture-sensitive synthetic splinting materials. Exemplary moisture-sensitive synthetic splinting materials are described in, for example, the following U.S. Pat. No. : 4,609,578 to Reed; U. S. Pat. No. 4,667,661 to Scholz et al.; U.S. Pat. No. 4,774,937 to Scholz et al.; and U.S. Pat. No. 5,027,803 to Scholz et al. These products are typically moisture-sensitive, i.e., exposure to moisture, including ambient humidity levels, causes these products to rapidly stiffen and form a cured splint or cast.

The requirements for packaging these products include a long shelf life —e.g., two years or more at ambient conditions—along with a package allowing easy dispensing of the product. These challenges are made more acute because the product is not typically refrigerated, but is instead typically stored at ambient temperature. For the above reasons, any package for use with these products preferably forms a hermetic seal which is moisture-impermeable.

Due to these stringent packaging requirements, these products have typically been sealed in single-use packages containing pre-cut lengths of the products. Such packaging, however, sometimes results in wasted product and packaging material, as well as increased costs associated with individually packaging each pre-cut length of casting/splinting material.

Attempts have been made to package these products in continuous length packaging to avoid the waste associated with pre-cut length packaging. U.S. Pat. No. 4,770,299 to Parker, U.S. Pat. No. 4,869,046 to Parker, and U.S. Pat. No. 4,899,738 to Parker all disclose a medical bandaging product packaged in an outer sleeve of a moisture-impermeable material such as an aluminum foil laminate. The moisture-proof outer sleeve package disclosed is essentially as long as the product contained therein. The packaged product is typically rolled up and placed in a box where it may be unrolled such that a portion of the package (with the product therein) may be cut to length. The remaining packaging material is then resealed after each use. This packaging system has the advantage of allowing the product to be cut to the particular length desired, but also has several disadvantages.

Among these disadvantages are that packaging the material as a roll in a box produces many creases in the relatively stiff aluminum foil laminate typically used to form the sleeve. The creases potentially are a source of pinholes which leak and cause premature curing of the product in the package. Also, because the entire length of the product must be enclosed in an outer wrap of the packaging material, a relatively large amount of packaging material is used which adds to the cost of the product.

One attempt to solve the problems associated with packaging the entire length of the product is disclosed in U.S. Pat. No. 5,003,970 to Parker et al. That patent discloses a continuous length splinting material packaged in an outer container formed of a moisture-impervious material. The bulk of the product is stored in an enlarged area of the package with an elongate dispensing sleeve extending from the enlarged area.

The package appears to include two side panels having an enlarged area and tapering to form the sides of the extended sleeve and a strip used to connect the sides of the package and form the top and bottom of the extended sleeve. As depicted in the drawings and described in the specification, this package is not easily manufactured using existing packaging equipment. In addition to the problems with the packaging, the patent also fails to disclose an effective and easy-to-use means of sealing the extended sleeve during and between uses.

Accordingly, known methods have proven less than desirable in use. The more secure of the devices are difficult to use which increases the amount of time the package is open during use, thereby allowing moisture to enter and harden the material therein. Conversely, the sealing methods which are easy to use form seals of questionable integrity which allow moisture penetration into the package even when the seal is closed.

One container that overcomes many of these problems is shown in U.S. Pat No. 5,505,305 to Scholz et al. Here, the container includes a magnetic closure coupled to the opening of an expandable pouch which contains moisture-sensitive product therein. The magnetic closure permits hermetic sealing of the pouch between uses. While highly effective, the invention of the '305 patent generally requires coupling of at least a portion of the magnetic sealing device to the pouch. Further, some moisture intrusion may occur when the magnetic closure is open, e.g., during dispensing.

SUMMARY

To overcome these obstacles, apparatus and methods for storing moisture-sensitive products such as moisture-curable orthopedic splinting/casting product are herein provided. Advantageously, the apparatus and methods of the present invention provide for storage of continuous length, moisture-sensitive products within flexible pouches. By folding the products in accordance with the present invention, resistance to product dispensing is substantially reduced. The folding patterns of the present invention further reduce curing due to inadvertent exposure to ambient conditions. Still further, the fold patterns described herein allow storage of product within a pouch having reduced length.

The present invention also provides closure systems that permit substantial sealing of the pouch during and after dispensing of the product. In some embodiments, the closure system includes a compression device that substantially conforms the pouch to the product both during and after dispensing. The compression device may also smooth the surfaces of the product as the latter is dispensed through an opening in a first end of the pouch. The closure system preferably also includes a sealing device to reseal the opening between uses. The sealing device, in one embodiment, is a parallel clamp that seals across the entire width of the opening simultaneously. Other embodiments of the invention are described below.

In one embodiment, an apparatus is provided. The apparatus includes a pouch having a first end, a second end, and a pouch length extending therebetween. The pouch further defines an interior. The apparatus further includes a moisture-sensitive product having a continuous length. The product is preferably folded into a packaged configuration having a plurality of sections arranged within the interior and along the pouch length. Each section includes at least two folds and a segment spanning therebetween, where the segment also extends along the pouch length.

In another embodiment, an apparatus for storing and dispensing a continuous length of product is provided. Here, the apparatus includes a pouch having an interior for receiving and storing a continuous length of moisture-sensitive product where the pouch includes a first end. A compression device adapted to couple to the pouch proximate the first end is also provided. The compression device includes a first compression member and a second, opposing compression member where the compression members are adapted to substantially conform the shape of the first end of the pouch to the shape of the product.

In yet another embodiment, a closure apparatus for use with products stored within a flexible pouch is provided. The closure apparatus includes a compression device having two opposing compression members and a sealing device operatively coupled to the compression device. The sealing device includes opposing sealing members wherein the sealing members are selectively movable between an open position and a closed position.

A method for packaging a continuous length of product in a pouch is also provided. In one embodiment, the method includes providing a continuous length of moisture-sensitive product. The product is folded into a packaged configuration having a plurality of interconnected sections where at least one section includes at least two folds and a segment spanning therebetween. The method further includes enclosing the plurality of sections within a pouch where the pouch includes a first end, a second end, and a pouch length extending therebetween and where the segment extends along the pouch length.

A method for dispensing a product from a flexible pouch is also disclosed. In one embodiment, the method includes providing a pouch containing a flexible product where the pouch has a first end. The method further includes coupling a closure apparatus to the pouch proximate the first end. The closure apparatus includes a compression device having two opposing compression members, and a sealing device having opposing sealing members. The sealing members are selectively movable between an open position and a closed position. The method also includes positioning the sealing device in the open position and creating a first opening proximate the first end of the pouch to provide access to the product therein. The product is then dispensed from the pouch through the first opening, wherein the compression members substantially conform the shape of the pouch to the shape of the product.

Although briefly summarized here, the invention can best be understood by reference to the drawings and the description of the exemplary embodiments which follow.

BRIEF DESCRIPTION OF THE DRAWINGS

The invention will be further described with reference to the drawings wherein like reference characters indicate like parts throughout the several views, and wherein:

FIGS. 5C–5E are enlarged partial section views of pouches having product folded in accordance with still other embodiments of the invention.

DETAILED DESCRIPTION OF EXEMPLARY EMBODIMENTS

In the following detailed description of the embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
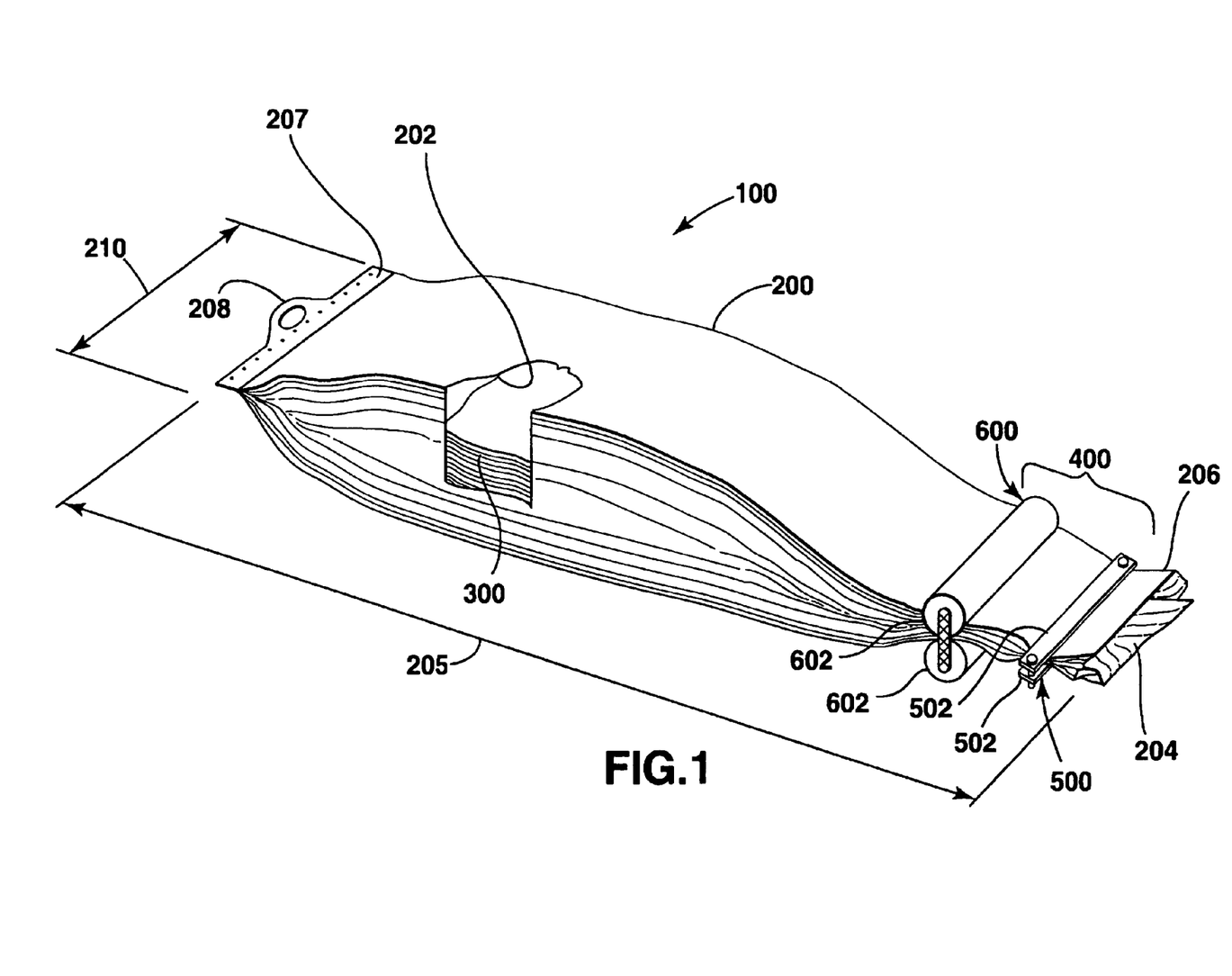
FIG. 1 is perspective, partial cut-away view of a pouch for storing a moisture-sensitive product in accordance with one embodiment of the invention.

FIG. 1 illustrates an apparatus 100 for packaging and storing a moisture-sensitive product in accordance with one embodiment of the invention. While described herein primarily with respect to moisture-curable orthopedic splinting/casting products, the invention is equally applicable to most any other moisture-sensitive product.

In the embodiment illustrated in FIG. 1, a sleeve or pouch 200, preferably elongate, made from a flexible and ideally moisture-impermeable material is provided. The pouch defines an interior space 202 which is accessed via an opening 204 located at a first end 206 of the pouch 200. A sheet of continuous length orthopedic splinting/casting product 300 (which is hereinafter referred to as "product" 300) is located within the interior 202. As illustrated more clearly in FIG. 2, the product 300 is folded so that, although it may have an unfolded length substantially greater than the length of the pouch 200, it fits easily therein when folded into a packaged configuration as shown.

An optional closure system 400 may also be provided and shown in FIG. 1. Preferably, the closure system includes a sealing device 500 (further described herein) and a compression device 600 (also further described herein). The closure device 500 and compression device 600 may be separate components as illustrated in FIG. 1 or, alternatively, may be combined to form an integrated closure system 400 as further described below. Regardless, the sealing device 500 is located proximate the pouch opening 204 to permit substantially hermetic sealing of the opening 204 during storage, i.e., when the product 300 is not being dispensed. The compression device 600 is similarly located proximate the opening 204 and is provided to reduce moisture intrusion during dispensing of the product 300 and may further reduce moisture intrusion when the sealing device 500 is closed.

Each major component of the apparatus 100 is described in more detail below.

Pouch

The pouch 200 (see FIG. 1) of the present invention may be manufactured using one piece of material, preferably a moisture-impervious material, folded over and heat sealed along the mating edges to form what is commonly referred to as a standard fin seal. Alternatively, two pieces of material may be heat-sealed together along their peripheral edges.

One preferred packaging material for the pouch 200 is a laminate with an outer layer of polypropylene over a layer of polyethylene over a layer of aluminum foil. The innermost layer is preferably SURLYN™ ionomer resin available from E.I. DuPont de Nemours & Company, Wilmington, Del., or, alternatively, a form of polyethylene to provide sufficient heat sealing properties.

In another embodiment, the pouch 200 may be formed with gussets (not shown) that permit the pouch 200 to expand more readily to accept the product 300. Such gussets are generally discussed in U.S. Pat. No. 5,505,305.

The pouch has a pouch length 205 (see FIG. 1) measured between the first end 206 and a second end 207. While shown and described herein as an elongate pouch having a constant width 210, pouches of most any shape are contemplated. For example, a pouch 200 having a length 205 equal to its width 210 or, alternatively, a pouch having a variable width along the length is possible without departing from the scope of the invention. In one exemplary embodiment, the pouch is generally rectangular in the plan view and has a length 205 at least two times the pouch width 210. Still other pouch configurations can be produced to correspond to the desired product to be stored therein.

Product

While the exact construction of the actual splinting/casting material is not central to an understanding of the present invention, exemplary materials are described in U.S. Pat. No. 4,667,661 to Scholz et al.; U.S. Pat. No. 4,774,937 to Scholz et al.; U.S. Pat. No. 5,027,803 to Scholz et al.; and U.S. Pat. No. 6,027,465 to Scholz et al.

Figure 2:
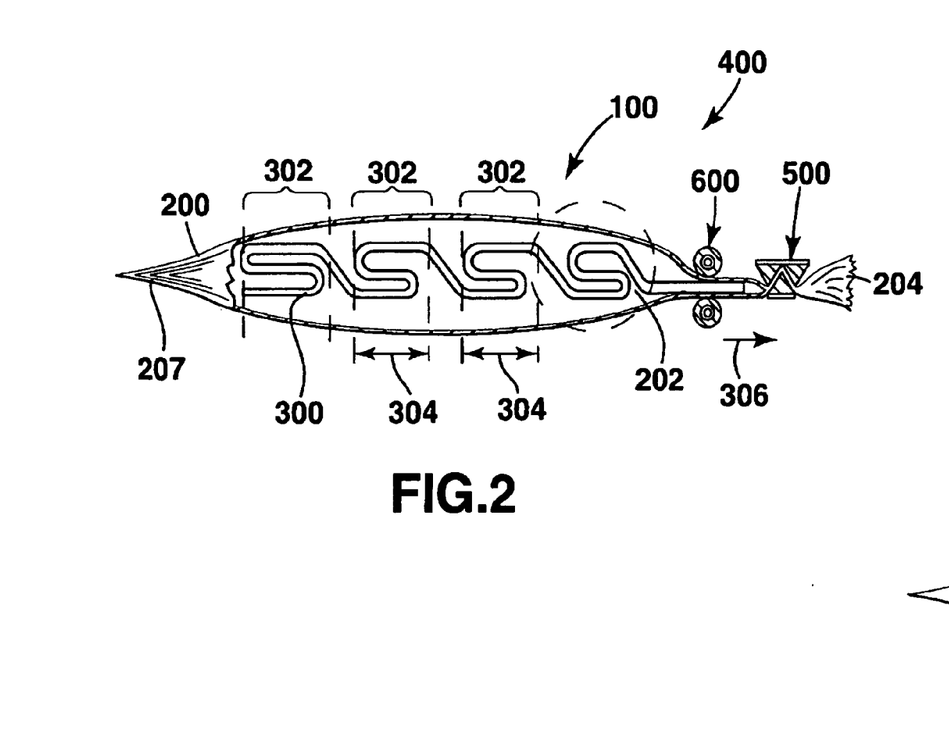
FIG. 2 is cut-away view of a pouch having product folded in accordance with one embodiment of the invention.

FIG. 2 illustrates a cut-away view of the apparatus 100. In this view, the folded product 300 is shown within the interior 202 of the pouch 200. Unlike other splint packaging systems where the product is generally enclosed within a pouch of equal length or, alternatively, where the product is rolled to fit within a pouch having an enlarged portion, the present invention folds the product into distinct, repeating sections 302 each having a length 304. When so folded, the product 300 may preferably fit into a generally flat pouch, e.g., a pouch that, when empty, forms a generally flat sheet. The flat pouch configuration is advantageous due to its relatively simple and cost-effective construction. However, pouches of most any shape are possible without departing from the scope of the invention.

Figure 3A:
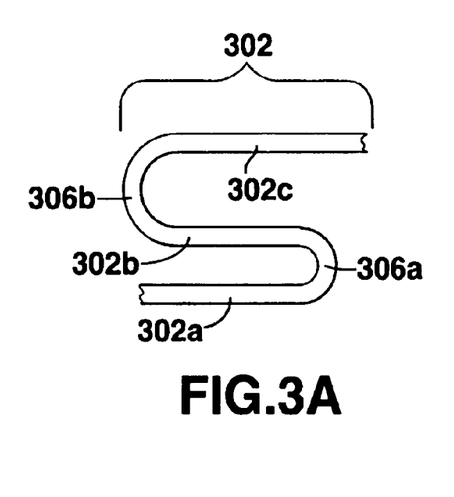
FIG. 3A is an enlarged partial view of a section of the moisture-sensitive product of FIG. 2.

While various packaged configurations, e.g., product folding patterns, are possible, the arrangement of the product 300 within the pouch 200 is preferably selected to permit easy withdrawal therefrom via the opening 204. The folding pattern is further selected to permit packaging of a given length of product within a substantially shorter pouch One folding configuration that achieves these objectives is shown in FIG. 2. Here, the product is folded to form a series of repeating S-shaped sections 302 along the length of the pouch 200. As shown in FIG. 3A, each section 302 includes a generally linear segment 302b spanning between two folds 306a and 306b. In this particular embodiment, connecting segments 302a and 302c form the remainder of the S-shaped section 302.

While the method used to fold the product 300 can be adapted to take advantage of specific manufacturing equipment or processes, it includes, in one embodiment, first positioning the product 300 to form connecting segment 302a. The product is then folded back on itself along fold 306a to form segment 302b. The product 300 is then folded back on itself again along fold 306b to form connecting segment 302c. Connecting segment 302c then connects to the beginning of connecting segment 302a of the next section (see FIG. 2) after which the S-shaped sections may repeat.

By folding the product along the length of the pouch in this manner, an approximately three-fold reduction in product length may be achieved. However, other embodiments having more (or less) sections can achieve greater (or lesser) packaging efficiencies. Preferably, when the product 300 is folded into a packaged configuration, e.g., as shown in FIG. 2, it can then be enclosed within the pouch 200 using conventional flow wrapping techniques.

It is noted that, for clarity, the product 300 is illustrated in the following figures with exaggerated separation between adjacent sections and segments (e.g., gaps between segments 302a/302b and 302b/302c). In practice, the segments may physically contact one another.

To remove a length of product 300 from the pouch 200, an end user simply pulls on the end of the product accessible through the opening 204 (with the closure device 500 open or otherwise removed). Since the segments 302a, 302b, 302c are generally aligned with the pulling direction 306 (see FIG. 2), the product 300 tends to unfold and egress more easily from the pouch than if the segments were otherwise oriented. Further, by orienting the segments 302a, 302b, and 302c along the length of the pouch 200, e.g., parallel with the pouch, a favorable (i.e., smaller) pouch height and length are achieved.

Other advantages of the sectioned, folding pattern of the present invention include, for instance, reduced frictional resistance during dispensing. This is attributable to the fact that the sections 302 provide less product surface in contact during dispensing than some other folding configurations such as the full-length fan-fold shown in FIG. 3B. Further, fold configurations like that described in FIG. 3A provide only a small portion of the product 300 proximate the opening 204 (see e.g., FIG. 2). Thus, premature curing of the product 300 due to inadvertent exposure via the opening 204 is limited to only that portion proximate thereto. Other embodiments, e.g., the horizontal fan-folds of FIG. 3B, may have numerous folds near the opening, increasing the risk of premature curing of portions of the product 300' along its entire length. In some instances, moisture intrusion into the pouch 200' may necessitate disposal of the entire product 300'.

While described in FIGS. 2 and 3A as S-shaped sections, other fold configurations are also possible. In general, any packaged configuration that provides discrete sections having one or more segments extending along the length of the pouch is possible, e.g., segments that are parallel to the pouch length or otherwise correspond with the dispensing direction. For purposes of explanation, the folding patterns are frequently defined herein without regard to the connecting segments (e.g., those segments such as 302a and 302c that interconnect one section 302 to the next). For instance, the folding configuration illustrated in FIG. 3A is said to include one segment 302b bounded by folds 306a and 306b. It is understood that, because each section 302 forms part of a continuous length of product 300, the connecting segments 302a and 302c are included by necessity. Accordingly, the following discussion may exclude specific reference to the connecting segments except where necessary to clarify the invention.

Figure 3B:
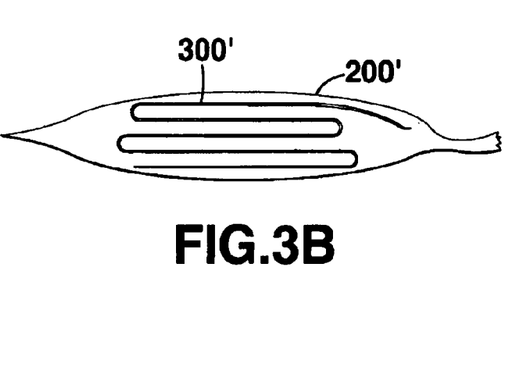
FIG. 3B is cut-away view of a pouch showing product in an alternative folding configuration.
Figure 4:
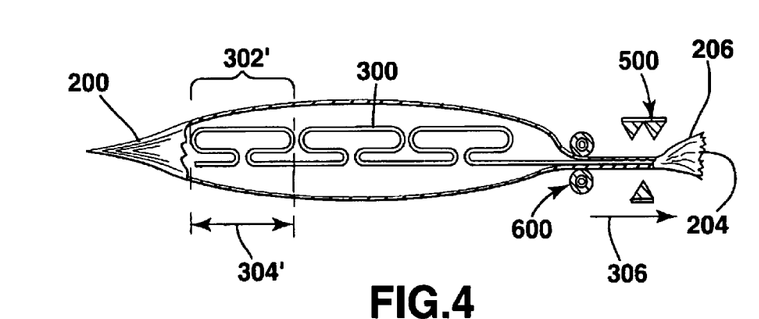
FIG. 4 is cut-away view of a pouch having product folded in accordance with yet another embodiment of the invention.
Figure 5A:
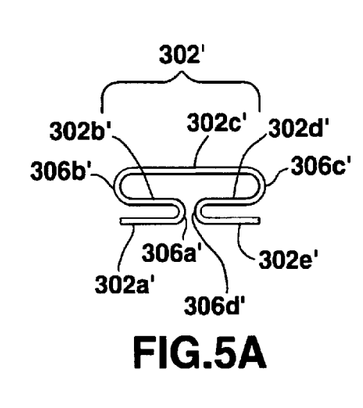
FIG. 5A is an enlarged partial view of a section of the product of FIG. 4.

Another example of a packaged configuration in accordance with the present invention is shown in FIGS. 4 and 5A. The folding arrangement illustrated in these figures, like that shown in FIGS. 2 and 3, provides discrete sections having segments extending along the length of the pouch 200. Unlike the embodiment of FIGS. 2 and 3A however, the product 300 is folded in a repeating series of mushroom-shaped sections 302' each having a length 304'.

FIG. 5A illustrates each section 302' having three segments 302b', 302c', and 302d' wherein each of these segments is bounded by folds. Segment 302b' is bounded by folds 306a' and 306b', segment 302c' is bounded by folds 306b' and 306c', and segment 302d' is bounded by folds 306c' and 306d'. Connecting segments 302a' and 302e' span between and connect adjacent sections. The sections 302' are, in one embodiment, formed by first positioning a connecting segment 302a' as shown in FIG. 5A. The product is then folded over on itself along fold 306a' to form segment 302b' which is preferably equal in length to connecting segment 302a'. The product 300 is then folded over onto itself again along fold 306b' to form segment 302c' which, in one embodiment, is approximately twice as long as segment 302b'. The product is thereafter folded under itself along fold 306c' to form segment 302d' and folded under itself again along fold 306d' to form connecting segment 302e' as shown. Segments 302d' and 302e' are approximately equal in length to segments 302b' and 302a', respectively.

As with the embodiments illustrated in FIGS. 2 and 3, removal of the product 300 in the direction 306 as shown in FIG. 4 causes the mushroom-shaped sections 302' to unfold and dispense through the opening 204. Because each section 302' has a minimal portion of the product 300 in contact, resistance to product removal is again reduced. Further, only a small length of product is proximate the opening 204, reducing the chance of inadvertent exposure and premature curing that could otherwise require disposal of all or a substantial portion of the product.

Figure 5B:
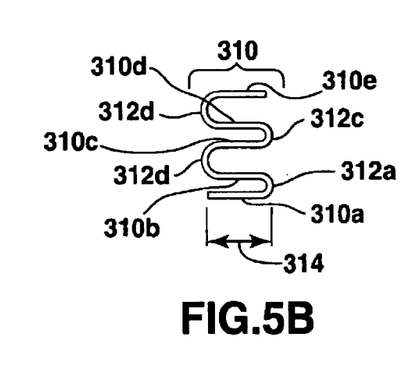
FIG. 5B is an enlarged partial view of a section of the product in accordance with yet another embodiment of the invention.

FIG. 5B illustrates yet another packaged configuration in accordance with the present invention. Like the embodiment illustrated in FIG. 5A, the section 310 of FIG. 5B has a length 314 and includes three segments 310b, 310c, and 310d each bounded by folds 312a and 312b, 312b and 312c, and 312c and 312d, respectively. Connecting segments 310a and 310e span between and connect adjacent sections 310. Where the segments 310a, 310b, 310c, 310d, and 310e are of equal length, the embodiment of FIG. 5B yields a packaged configuration approximately one fifth the length of the unfolded product 300.

While the length of each section 302 (see FIG. 3A), 302' (see FIG. 5A), and 310 (see FIG. 5B) may vary, each section preferably has an unfolded length that corresponds to a common splinting/casting size. For instance, each section may have an unfolded length of about 30 inches to about 60 inches (75–150 centimeters). In addition, the pouch size is preferably selected to enclose a convenient number of sections. For example, in one embodiment, the continuous length product 300 is about 12 to about 15 feet (3.5–4.5 meters) long and folded into three to six sections so that it fits within a pouch 200 that ranges from about 2 to about 5 feet (0.5–1.5 meters) long. Additional pouch length may be required to accommodate pouch expansion and product folding and dispensing as further explained below. Preferably, the ratio of the product length to the pouch length is about 2:1 or more and more preferably about 3:1 or more. The pouch itself may further be folded, preferably once, to fit within a shipping or storage box that is about 10 to about 30 inches (25–75 centimeters) long. Of course, other pouch and box sizes are also contemplated.

Figure 5C:
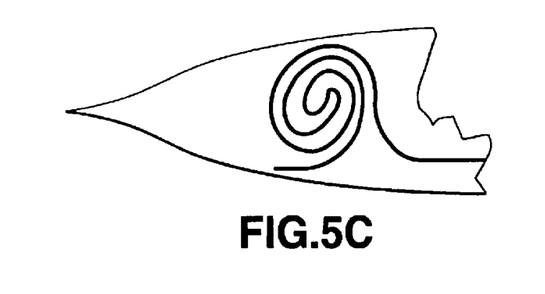
FIG. 5C shows a rolled configuration.
Figure 5D:
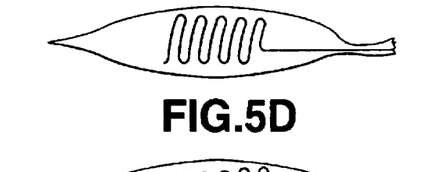
FIG. 5D shows a tilted fan-fold configuration.
Figure 5E:
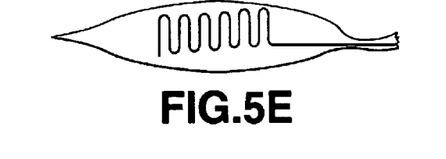
FIG. 5E shows a vertical fan-fold configuration.

Still other folding configurations are shown in FIGS. 3B and 5C–5E. FIG. 3B shows a product in a horizontal fan-fold. FIG. 5C illustrates a product having rolled sections; FIG. 5D shows a product folded in a tilted fan-fold; and FIG. 5E shows a product folded in a vertical fan-fold. While the above-described embodiments illustrate the product 300 dispensed in a horizontal direction, e.g., the pouch 200 is horizontal, the invention is equally advantageous when dispensing vertically. In such cases, the apparatus 100 may be suspended such that the opening 204 (see FIG. 1) is at a lower elevation than the second end 207. To accommodate vertical dispensing, the pouch 200 may include a suspension member, e.g., an eyelet 208 (also shown in FIG. 1) or a hook (not shown). The suspension feature is located on the pouch, e.g., at the second end 207 opposite the opening 204, and is adapted to support the apparatus 100 from a corresponding hanging feature, e.g., hook (not shown) or the like. Alternatively, the pouch may be draped over a rod. The closure system 400, in addition to its other uses as described below, prevents the product 300 from falling out of the pouch when the latter is vertically positioned.

Closure System

Referring once again to FIG. 1, the apparatus 100 may preferably include the optional closure system 400. One purpose of the closure system 400 is to permit sealing of the opening 204, thus reducing moisture intrusion into the interior 202 of the pouch 200.

To seal the opening 204 before and after dispensing, a sealing device 500 is provided. The sealing device 500 is placed over the first end 206 of the pouch 200 and, when in a closed configuration, clamps shut or otherwise substantially hermetically seals the opening 204. While most any device capable of sealing the pouch is possible, one exemplary embodiment is shown in FIG. 1. Here, the device 500 includes two elongate elements 502 that span across the top and bottom of the pouch 200 proximate the opening 204. The ends of the elements 502 include a fastening device, e.g., clip or fastener, which permits tightening of the elements relative to one another. For convenience, proximate ends of the opposing elements 502 may be coupled, e.g., hinged, to secure the two elements to one another. To further improve sealing, the device 500, in another embodiment, includes interengaging teeth (see FIG. 2). Other devices that permit substantial sealing of the pouch are also possible including for example, biased (magnetic, spring-loaded, etc.) clamps, tongue and groove scissors clamps, moisture-proof adhesive tapes, spring-loaded compression gaskets, leverage clamps, screw action devices, ZIPLOCK™—type seals, etc.

While the sealing device 500 seals the pouch 200 before and after dispensing, the device 500 is opened or otherwise removed from the pouch during use (i.e., dispensing) and, thus, is unable to prevent moisture intrusion during that time. For this reason, the closure system 400 preferably includes a compression device 600 of which one embodiment is diagrammatically illustrated in FIGS. 1 and 2. The compression device 600 illustrated in these figures is configured as two opposing compression members, e.g., cylinders 602, which substantially conform the shape of the first end 206 of the pouch 200 to the shape of the product 300. Conformance occurs by urging the walls of the pouch 200 against the product 300 under the compressive force of the members 602.

Figure 6:
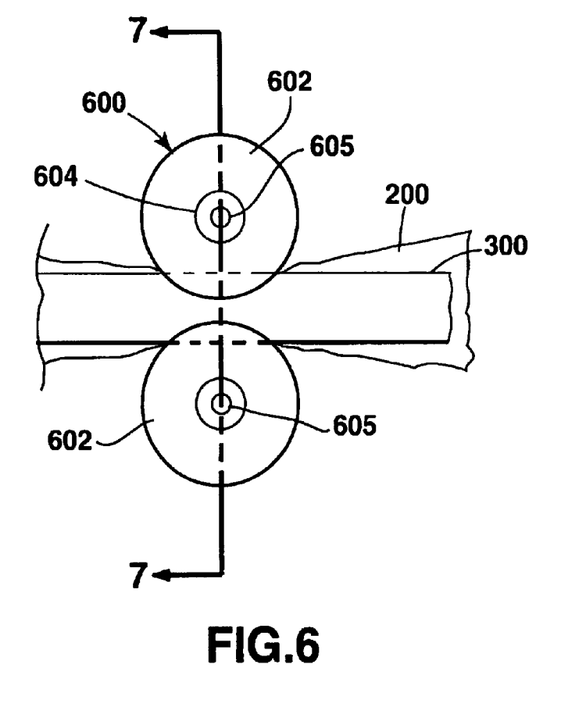
FIG. 6 is an enlarged view of a compression device in accordance with one embodiment of the invention.
Figure 7:
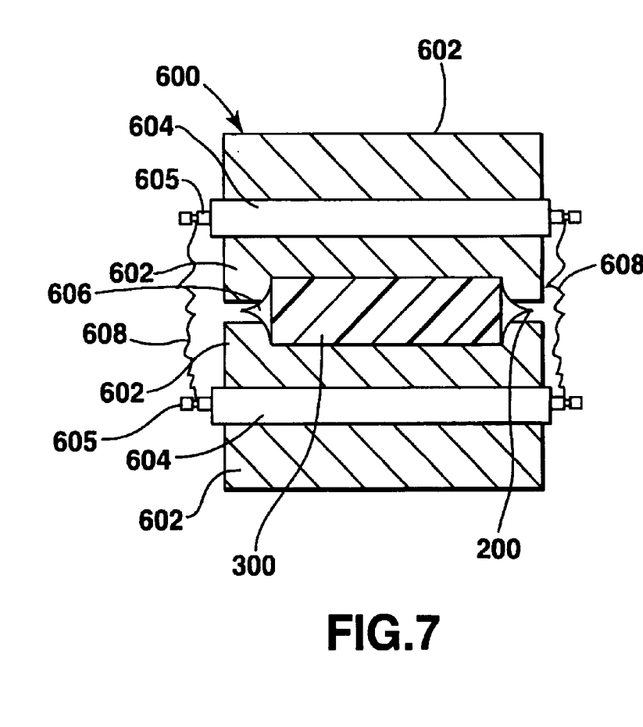
FIG. 7 is a section view taken along line 7—7 of FIG. 6.

FIGS. 6 and 7 provide a more detailed view of a compression device 600 according to one embodiment of the invention. To adequately conform to the shape of the product 300, the members 602 preferably include or are made from compressible material. The compressible material permits deformation of the members 602 (see FIG. 7) such that sealing around the periphery of the product 300 is achieved. In some embodiments, only one of the members 602 may be compressible, although it is preferred that both members 602 are compressible. While the members 602 can be made of most any compressible material, they are, in one embodiment, made of low density foam pads. Low density foam provides a member having a high compression ratio which, in turn, allows the members to deform and better conform to the contours of the product 300. The pads which form the members 602, as further explained below, are not limited to cylindrically shaped elements but may be most any shape.

To ensure adequate sealing along the side edges of the product 300, the members 602 preferably extend outwardly beyond the transverse edges of the product (see FIG. 7). This construction permits the members 602 to better wrap around the transverse edges and minimize the gap 606 available for moisture entry. Alternatively, the device 600 may include side compression members (not shown) that, similar to members 602, apply a transverse compressive load to seal against the side edges of the product.

The contour conformance illustrated in FIG. 7 can be achieved in a variety of ways. For instance, a uniform diameter member 602 may be pressed against the pouch 200 with sufficient force to deform as shown. In another embodiment, the members 602 may be somewhat less compressible but have a stepped profile (similar to that shown in FIG. 7) that conforms to the shape of the product. Still further, the members 602 may achieve conformance through a combination of material selection (e.g., low density foam) and contoured (e.g., stepped) construction.

To ensure the compressible members 602 maintain adequate preload against the product 300, each member 602 preferably includes a rigid or semirigid member, e.g., core 604, to which the member 602 is formed or otherwise attached. The core 604 ensures that the members 602 provide the desired compression across their length. The cores 604 also preferably include a structural feature that permits connecting of the proximate ends of opposing cores 604. In one embodiment, the structural feature is merely an extended portion of the core, e.g., a tip portion 605, attached to or integral with each end of the core 604. While the core 604 is shown as a unitary member, other embodiments are also possible, e.g., an axle and/or bearings, multiple cores, external support members instead of cores, etc.

A tension member is provided to bias the members 602 towards one another. In one embodiment, the tension member is a dynamically elastic component 608, e.g., a rubber band or spring, as diagrammatically shown in FIG. 7. However, the tension member may also be configured as a semi-rigid, rigid, or other elastic member. The length and compliance of the tension members 608, the compliance of the members 602, and other factors determine the deformation of the members 602. These variables are pre-selected to ensure that the members 602 substantially conform to the contours of the product 300 and further to ensure the desired preload is applied.

In use, the compression device 600 is positioned external to the pouch proximate the first end 206 as shown in FIG. 1. The product 300 is positioned so that it extends between the members 602 (as shown in FIGS. 2 and 6). Where necessary, the device 600, e.g., the tension member 608, may be adjusted to increase or decrease the desired compression of the members 602.

During dispensing, the product 300 moves past the device 600 as it is pulled in the direction 306 (see FIG. 2). As the product moves, the members 602 may spin about the core 604 or, more preferably, they may remain fixed, i.e., do not rotate.

Once the desired length of product passes through the opening 204, the product is cut and the remaining product is pushed back into the pouch so that the sealing device 500 may be closed. Optionally, the pouch may also be cut in conjunction with the product. In this case, the compression device 600 may be moved along the length of the pouch as required to maintain proximity with the opening 204. The device 600 may include other devices, e.g., a clamp (not shown), to selectively secure the device 600 along the length of the pouch 200.

In addition to conforming the pouch 200 to the product 300, the compression device 600 also tends to smooth the product 300 during dispensing. That is, as the product is dispensed, it is squeezed between the members 602. This squeezing action may result in removal of wrinkles and/or tend to straighten folds formed in the product 300. To increase the smoothing effect, the length of the members 602 along the pouch, e.g., the length of contact between the members 602 and the product 300, may be increased.

While the closure system 400 is shown' and described above as including a separate and distinct compression device 600 and sealing device 500, other embodiments combine the devices into an integral closure system. For example, FIGS. 8 and 9 illustrate a closure apparatus 800 that includes a fixed frame having a compression device 802 and sealing device 804.

Figures 8, 9:
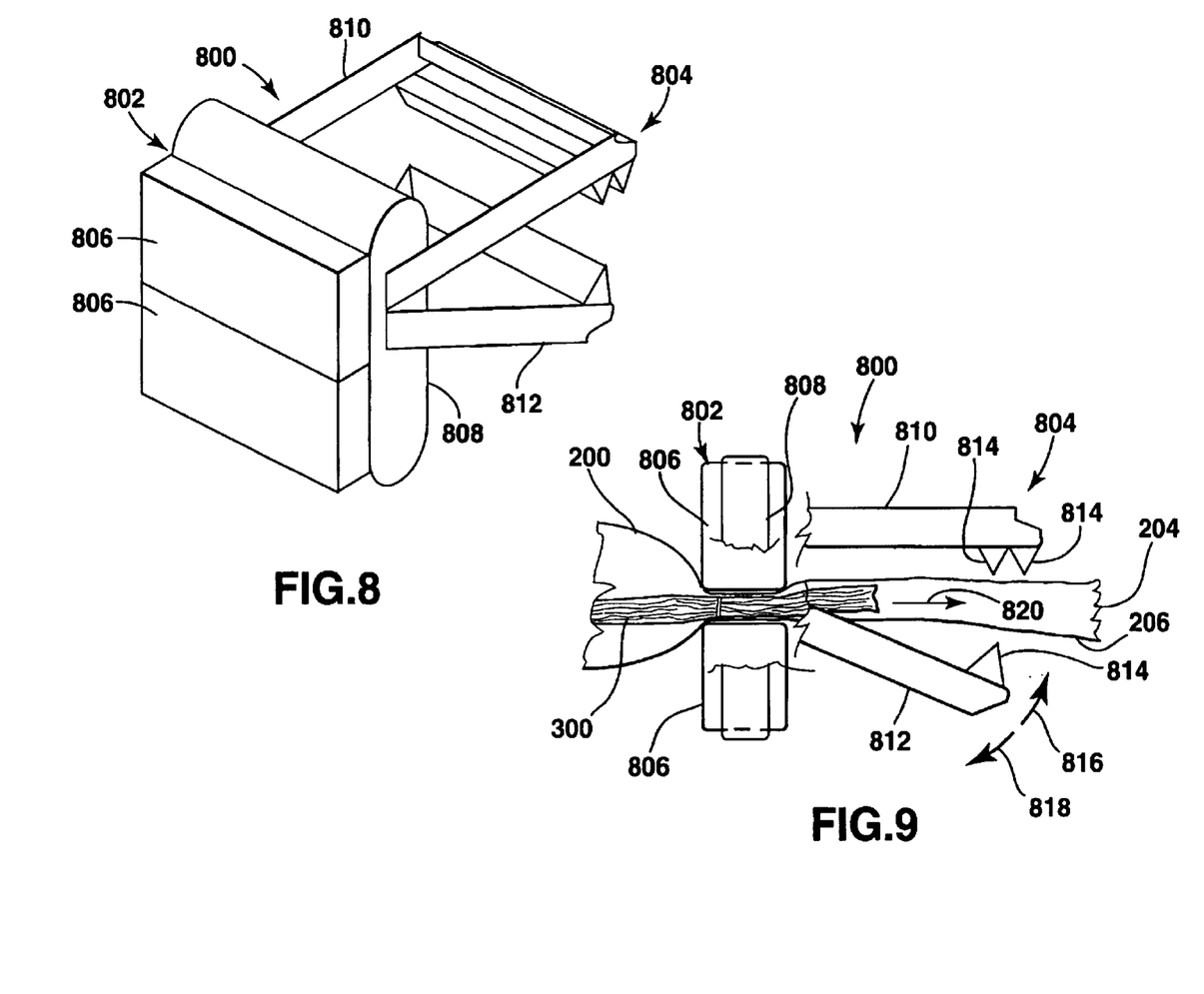
FIG. 8 is a perspective view of a closure apparatus in accordance with one embodiment of the invention.
FIG. 9 is a side elevation view of the closure apparatus of FIG. 8 with part of the apparatus removed for clarity.

The compression device 802 includes two compression members 806 that, in this exemplary embodiment, are rectangular in shape (see FIG. 9). However, other cross-sectional shapes including but not limited to, oval, circular and polygonal shapes are also possible without departing from the scope of the invention.

A frame assembly 808 couples the members 806 to one another. While not shown, the frame assembly 808 may include cores similar to cores 604 illustrated in FIG. 7 to support the members 806 or, alternatively, may externally support the members 806. In still another embodiment, the members 806 may be adhesively attached to the frame assembly 808. Extending away from the frame assembly 808 are arm members 810 and 812 which, at their distal ends, form the sealing device 804, preferably having interengaging teeth 814. To engage the teeth 814 and seal the pouch 200, the member 812 pivots about the assembly 808 as generally indicated by arrow 816 in FIG. 9. When the member 812 is pivoted in the direction 816, the pouch 200 is pinched between the teeth 814, effectively sealing the first opening 204. To open the sealing device 804, the member 812 is pivoted in a second direction as indicated by arrow 818 in FIG. 9.

The member 812 can be configured in a variety of ways. For instance, the member 812 may be biased (either in the direction 816 or 818) about the assembly 808. In another embodiment, the member 812 is plastically deformable about the assembly 808 in the directions 816 and 818 by the application of sufficient force. In still other embodiments, the apparatus 800 includes additional hardware, e.g., clips, or fasteners, adapted to secure the member 812 relative to the member 810 (e.g., hold the sealing device closed or open).

In use, the apparatus 800 is placed onto the first end 206 of the pouch 200 and positioned so that the product 300 is between the members 806 (see FIG. 9). Once again, the members 806 are preferably foam or a similar compressible material so that the members 806 substantially conform to the shape of the product 300 (see e.g., FIG. 7). Further, the members 806 preferably extend beyond the width of the product (see FIG. 7) to allow better sealing around the transverse edges.

Once the apparatus 800 is in place as shown in FIG. 9, the member 812 can be manipulated to close and seal the pouch. To dispense product, the member 812 is moved in the direction 818 and the product is pulled in the direction 820. When the desired length of product 300 has been dispensed from the pouch and severed from the remaining product, the remaining product can be tucked back into the opening 204 a sufficient distance to allow the sealing device 804 to seal the pouch 200. That is, the product 300 may be pushed back into the pouch 200 as shown in FIG. 9 so that the member 812 may be manipulated in the direction 816 to seal the opening 204 without interference from the product 300. As with the other embodiments described above, the pouch 200 may be cut with the product in which case the device 800 can be relocated along the pouch length to maintain the desired proximity to the opening 204.

Figures 10, 11:
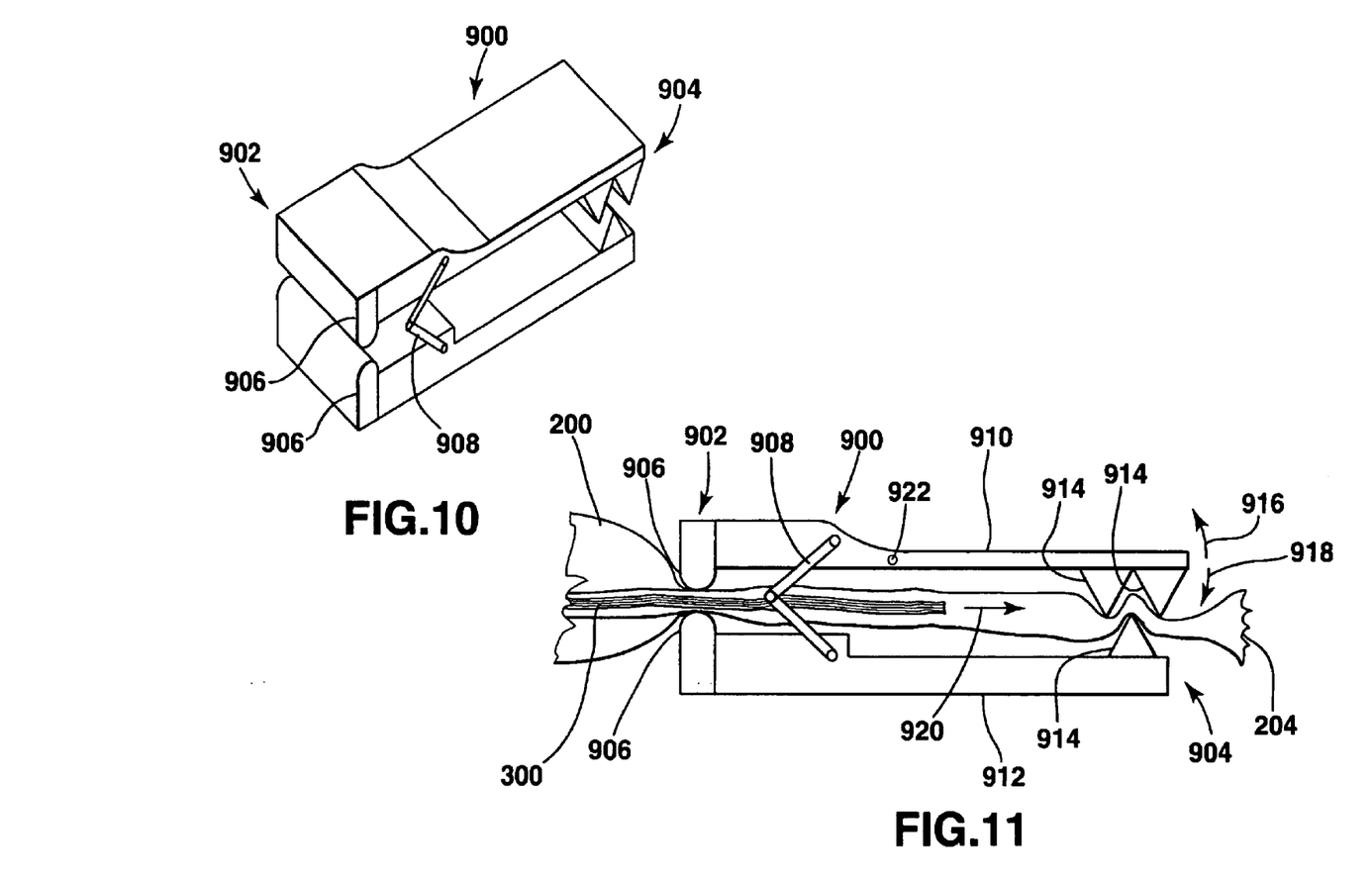
FIG. 10 is a perspective view of a closure apparatus in accordance with another embodiment of the invention.
FIG. 11 is a side elevation view of the closure apparatus of FIG. 10.

FIGS. 10 and 11 illustrate yet another embodiment of a closure apparatus 900. Like the apparatus 800, the apparatus 900 includes both a compression device 902 and a sealing device 904. In this particular embodiment, however, the apparatus 900 is configured to somewhat resemble a conventional clothes pin. In particular, the compression members 906, are biased towards one another by a torsion spring or other biasing member 908. Extending away from the compression device 902 are members 910 and 912. The distal ends of the members 910 and 912 form the sealing device 904. Like the sealing device 804 illustrated in FIG. 9, the sealing device 904, in one embodiment, includes interengaging members, e.g., teeth 914. To seal the pouch, the member 910 is moved in the direction 918 (see FIG. 11). To open the pouch, the member 910 is moved in the direction 916 (see FIG. 11). In one embodiment, movement of the member 910 is accomplished by plastic deformation, e.g., bending of the member 910. However, other embodiments where the members 910 and 912 move relative to one another by other methods, e.g., pivoting of the member 910 about an axis 922, are also possible.

In use, the apparatus 900 operates substantially like the apparatus 800 illustrated in FIGS. 8 and 9. To dispense product 300, the sealing device is opened and the product is pulled in the direction 920 (see FIG. 11). The members 906, which are preferably pads made of foam or another compressible material, conform to the shape of the product under the biasing load of the spring 908. Once the desired length of product is dispensed, it is cut and the product tucked back into the pouch so that the sealing device 904 may be closed, e.g., the member 910 moved in the direction 918. Optionally, the pouch may also be pulled between the members 906 so that it may be cut and shortened as the product is dispensed. In this case, the apparatus 900 may be moved along the length of the pouch as required to maintain proximity with the opening 204.

Container

Figure 12:
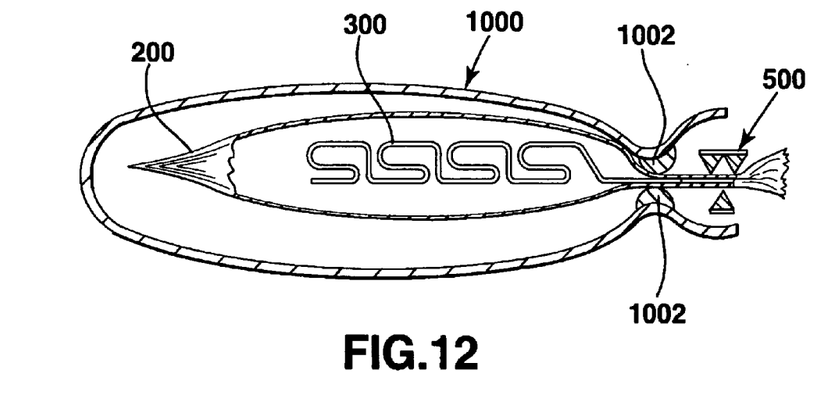
FIG. 12 is a section view of a pouch container in accordance with one embodiment of the invention.

FIGS. 12–20 illustrate still other embodiments for storing and dispensing product 300 in accordance with the present invention. In particular, FIG. 12 shows a pouch 200 containing product 300 as already described herein. However, the pouch 200 in this embodiment is further enclosed within a container 1000. The container 1000 is advantageous for several reasons such as providing greater protection to the pouch during shipping and storage. The container is preferably formed from a rigid or semi-rigid material such as plastic, metal, or cardboard. Integral with or otherwise coupled to the container 1000 are compression members 1002 which, like the compression members 602, 806, and 906 described above, are compressible and adapted to conform to the shape of the product 300. The container 1000 may include features, e.g., fasteners, suction cups, velcro, etc. (not shown), which permit attachment of the container 1000 to a counter or wall. A sealing device 500 as already described herein is also included.

Figure 13:
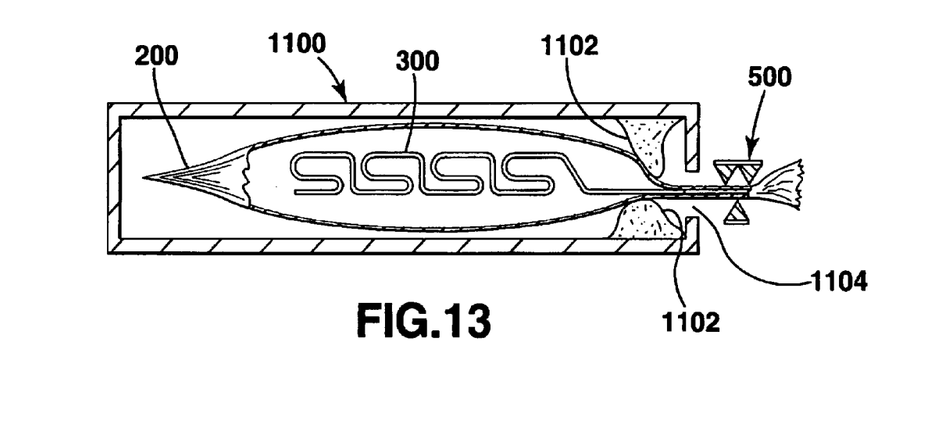
FIG. 13 is a section view of a pouch container in accordance with another embodiment of the invention.

FIG. 13 illustrates the pouch 200 (holding product 300) in a container 1100 similar to the container 1000. However, here the container may be formed from a conventional shipping container, e.g., a cardboard box. The box 1100 includes compression members 1102 that are coupled to the box and apply the desired compressive load to seal the interior of the pouch from ambient conditions. A sealing device 500 is also included.

Figures 14, 15, 16, 17, 18:
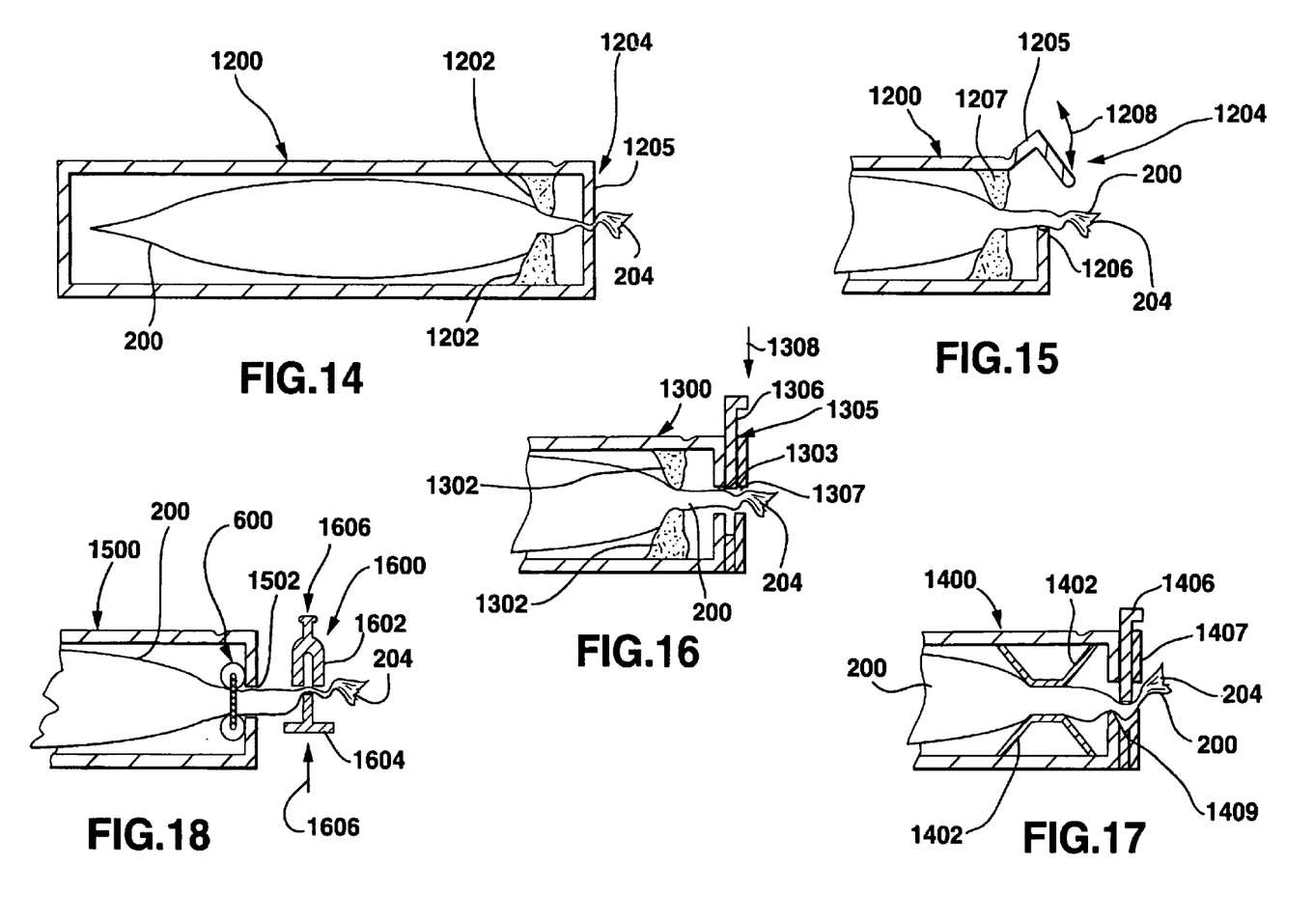
FIG. 14 is a section view of a pouch container in accordance with yet another embodiment of the invention showing the sealing device closed.
FIG. 15 is a partial section view of the container of FIG. 14 showing the sealing device open.
FIG. 16 is a partial section view of a container in accordance with still another embodiment of the invention showing the sealing device open.
FIG. 17 is a partial section view of a container in accordance with yet another embodiment of the invention showing the sealing device closed.
FIG. 18 is a partial section view of a container and separate sealing device in accordance with yet still another embodiment of the invention.

FIGS. 14 and 15 illustrate a container 1200 in accordance with yet another embodiment of the invention. While the container 1200 is substantially similar to the container 1100 of FIG. 13 in many respects (see e.g., compression members 1102 and 1202), the container 1200 further includes an integral sealing device 1204. The device 1204 includes, in one embodiment, an L-shaped member 1205 which pivots between a closed position which seals the first opening 204 of the pouch 200 (see FIG. 14) and an open position which provides access to the first opening (see FIG. 15). To maintain the L-shaped member in its closed position, a retaining feature such as a flexible lip 1206 is included.

The L-shaped member 1205 pivots about a pivot axis 1207. The pivot axis 1207 can be an actual hinged joint or alternatively, it can be a weakened portion of the container 1200 (e.g., a fold line in a cardboard box or a thinned section in a plastic container). In any event, the L-shaped member 1207 is movable in the direction 1208 to permit opening and sealing of the pouch 200.

FIGS. 16 and 17 illustrate yet additional embodiments of the invention. FIG. 16 illustrates a container 1300 similar in most respects to the container 1200 of FIGS. 14 and 15 (see e.g., compression members 1302). However, the embodiment illustrated in FIG. 16 replaces the L-shaped member 1205 with a guillotine-style sealing device 1305. The sealing device 1305 includes a slide member 1306 which rides within a guide slot 1307 formed by parallel portions of the container 1300. When the slide is raised (as shown in FIG. 16), access to the interior of the pouch is provided via the opening 204 and container aperture 1303. However, when the slide 1306 is displaced in the direction 1308, the slide traps the pouch 200 between the slide and a clamp surface, e.g., interior surfaces of the slot 1307, sealing the pouch 200.

FIG. 17 illustrates a container 1400 modified slightly from the container 1300 of FIG. 16. Here, a slide member 1406, when closed, pinches the pouch 200 against an opposing clamp surface 1409.

To secure the slide 1406 (or 1306) in the desired position, the slide may engage the slot 1407 (or 1307) with an interference fit. In embodiments where the container is made of a less rigid material, e.g., cardboard, the slide 1406 (or 1306) and the portions of the container that define the slot may be coated or reinforced to provide improved stiffness and wear resistance.

FIG. 17 further illustrates compression members 1402. In this particular embodiment, the compression members are cardboard extensions of a cardboard container 1400 rather than separate foam or other compressible material attached to the container. By sizing the cardboard extensions appropriately, the desired compression force may be applied against the product within the pouch 200.

FIG. 18 illustrates yet another embodiment of a container 1500. The container 1500 includes an independent compression device 600 (similar to that shown in FIGS. 6 and 7) and an independent sealing device 1600. The device 600 may be coupled to the pouch 200 before placement of the pouch into the container 1500.

Figure 19:
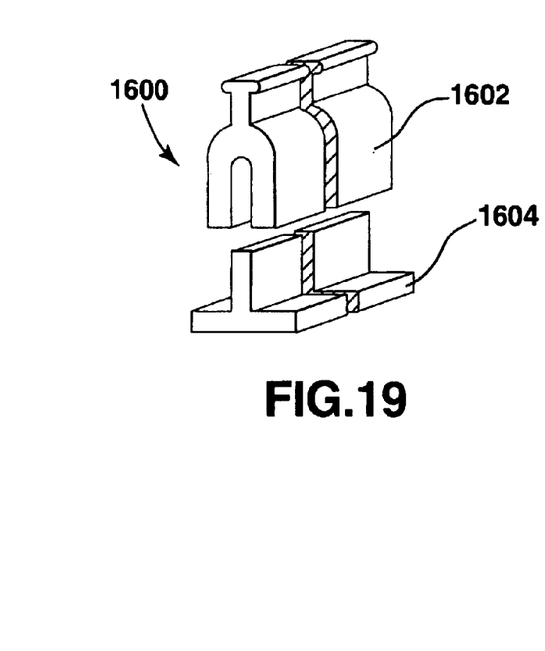
FIG. 19 is an enlarged partial view of a parallel sealing device in accordance with one embodiment of the invention.

The sealing device 1600, as shown more clearly in FIG. 19, includes a female member 1602 and a male member 1604. When sealed, the male member 1604 is aligned with the female member 1602 and the two components are forced together in the direction 1606 as shown in FIG. 18, trapping the pouch 200 therebetween. With the pouch trapped, the female member 1602 and the male member are engaged in an interference fit. Preferably, the sealing device 1600 includes an interconnecting member (not shown) which couples the members 1602 and 1604 to one another. Because the compression device 600 and the sealing device 1600 are independent of the container 1500, the embodiment of FIG. 18 permits the end user to dispense product either from the container (via an aperture 1502 as shown) or, alternatively, to remove the pouch 200 therefrom and dispense product directly from the pouch (see e.g., FIGS. 1 and 2). When dispensed from the container 1500, the device 600 is pulled against the wall of the container (see FIG. 18) as the product is removed from the opening 204.

One advantage of the sealing devices 804 (see FIG. 9), 904 (see FIG. 11), 1600 (See FIG. 19), and those shown in FIGS. 14–17 is that they are Is parallel closure devices. That is, these sealing devices seal across the width of the pouch simultaneously as opposed to scissors or zipper-type clamps in which the sealing members close gradually across the pouch width. Parallel closure devices may provide a more uniform seal and generally result in reduced bunching and creasing of the pouch proximate the sealing area Nonetheless, other parallel and non-parallel sealing devices may be used without departing from the scope of the invention.

Conclusion

Figure 20:
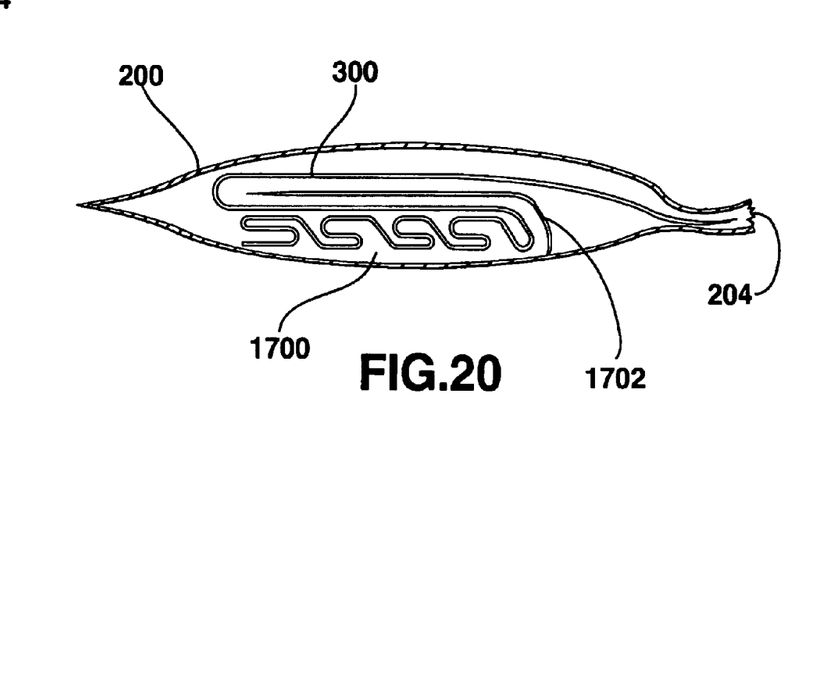
FIG. 20 is a section view of a pouch for holding moisture-sensitive product in accordance with still yet another embodiment of the invention.

While the present invention is described in terms of specific embodiments, other configurations are certainly possible. For example, to further protect the product 300 within the pouch 200 from moisture, the pouch may include a pocket 1700, an example of which is illustrated in FIG. 20. The pocket 1700 is formed by a member 1702 that is preferably attached to the pouch 200. The pocket 1700 protects the product 300 by providing yet another barrier between the product 300 and the ambient environment. While illustrated with only one pocket and simple S-shaped sections, the pocket 1700 may also accommodate other repeating sections such as the mushroom-shaped sections described above or even simple fan-folded products. Alternatively, a pouch having numerous pockets 1700 to accept individual sections, e.g., sections 302 of FIG. 2, is also contemplated.

The embodiments of the compression devices and sealing devices described herein are also exemplary. Any of the above-described compression devices or their equivalents may be interchanged with most any of the sealing devices described herein (or equivalents) to produce yet additional closure systems.

Advantageously, the present invention provides apparatus and methods for storing continuous length, moisture-sensitive products within flexible pouches. By folding the products in accordance with the present invention, resistance to product removal is substantially reduced. The folding patterns of the present invention further reduce curing due to inadvertent exposure to ambient conditions. Still further, the folding patterns described herein allow storage of product within an economical pouch having reduced length. The present invention also provides closure systems that permit substantial sealing of the pouch before, during, and after dispensing of the product.

The complete disclosure of the patents, patent documents, and publications cited herein are incorporated by reference in their entirety as if each were individually incorporated.

Exemplary embodiments of the present invention are described above. Those skilled in the art will recognize that many embodiments are possible within the scope of the invention. Variations, modifications, and combinations of the various parts and assemblies can certainly be made and still fall within the scope of the invention. Thus, the invention is limited only by the following claims, and equivalents thereto.

What is claimed is:

1. An apparatus, comprising:
   a pouch comprising a first end, a second end, and a pouch length extending therebetween, wherein the pouch further defines an interior; and
   a moisture-sensitive product having a continuous length, the product being folded into a packaged configuration comprising a plurality of sections arranged within the interior and along the pouch length, each section comprising at least two folds and a segment spanning therebetween, the segment also extending along the pouch length.

2. The apparatus of claim 1, wherein the pouch further comprises an opening proximate the first end, the opening permitting access to the interior of the pouch.

3. The apparatus of claim 1, wherein at least two of the sections are generally identical.

4. The apparatus of claim 1, wherein the pouch comprises at least one sheet of moisture-impervious material.

5. The apparatus of claim 1, wherein the continuous length product has a length at least two times the pouch length.

6. The apparatus of claim 2, further comprising a compression device proximate the opening.

7. The apparatus of claim 6, wherein the compression device is located on an exterior of the pouch.

8. The apparatus of claim 6, wherein the compression device comprises two opposing and compressible members biased towards one another.

9. The apparatus of claim 8, wherein each compression member comprises a foam pad.

10. The apparatus of claim 6, wherein the compression device is adapted to substantially conform the shape of the pouch to the shape of the product.

11. The apparatus of claim 2, further comprising a sealing device proximate the opening.

12. The apparatus of claim 1, wherein the pouch comprises a pouch width measured transversely to the pouch length, wherein the pouch width is substantially constant along the pouch length.

13. The apparatus of claim 1, wherein at least two sections each comprise only two folds and one segment therebetween.

14. The apparatus of claim 13, wherein the at least two sections each form an S-shape.

15. The apparatus of claim 1, wherein at least two sections each comprise three segments, each of the segments being bounded at both ends by folds.

16. The apparatus of claim 15, wherein at least two of the three segments are substantially equal in length.

17. The apparatus of claim 15, wherein each of the three segments are substantially equal in length.

18. The apparatus of claim 15, wherein each section comprises at least four folds.

19. The apparatus of claim 15, wherein the at least two sections each form a mushroom-shape.

20. The apparatus of claim 1, further comprising a suspension member.

21. The apparatus of claim 20, wherein the suspension member is located proximate the second end.

22. An apparatus, comprising:
   a pouch comprising a first end, a second end, and a pouch length extending therebetween, wherein the pouch further defines an interior; and
   a moisture-curable orthopedic splinting/casting product having a continuous length, the product being folded into a packaged configuration comprising a plurality of sections arranged within the interior and along the pouch length, each section comprising at least two folds and a segment spanning therebetween, the segment also extending along the pouch length.

23. An apparatus for storing and dispensing a continuous length of product, the apparatus comprising:
   a pouch comprising an interior for receiving and storing a continuous length of moisture-sensitive product, wherein the pouch further comprises a first end and an opening proximate the first end, the opening permitting access to the product within the interior of the pouch;
   a parallel closure sealing device adapted to substantially seal the opening; and
   a compression device adapted to couple to the pouch proximate the first end, the compression device comprising a first compression member and a second, opposing compression member, the compression members adapted to substantially conform the shape of the first end of the pouch to the shape of the product.

24. The apparatus of claim 23, wherein the parallel closure device comprises a male member and a female member, the female member adapted to receive the male member such that the pouch is trapped therebetween.

25. An apparatus for storing and dispensing a continuous length of product, the apparatus comprising:
   a pouch comprising an interior for receiving and storing a continuous length of moisture-sensitive product, wherein the pouch further comprises a first end;
   a suspension member coupled to the pouch; and
   a compression device adapted to couple to the pouch proximate the first end, the compression device comprising a first compression member and a second, opposing compression member, the compression members adapted to substantially conform the shape of the first end of the pouch to the shape of the product.

26. The apparatus of claim 25, wherein the suspension member is located proximate a second end of the pouch.

27. An apparatus for storing and dispensing a continuous length of product, the apparatus comprising:
   a pouch comprising an interior for receiving and storing a continuous length of moisture-sensitive product, wherein the pouch further comprises a first end and an opening proximate the first end, the opening permitting access to the product within the interior of the pouch; and
   a compression device adapted to couple to the pouch proximate the first end, the compression device comprising a first compression member and a second, opposing compression member the compression members adapted to substantially conform the shape of the first end of the pouch to the shape of the product as the product is dispensed from the pouch through the opening.

* * * * *

UNITED STATES PATENT AND TRADEMARK OFFICE
CERTIFICATE OF CORRECTION

PATENT NO. : 6,981,590 B1  
APPLICATION NO. : 09/551706  
DATED : January 3, 2006  
INVENTOR(S) : Ubel, F. Andrew, III Page 1 of 1

It is certified that error appears in the above-identified patent and that said Letters Patent is hereby corrected as shown below:

Column 2 – Line 28 - Delete "Pat" and insert - - Pat. - -, therefor.

Column 6 – Line 22 - After "pouch" insert - - . - -.

Column 8 – Line 39 - Delete "SD" and insert - - 5D - -, therefor.

Column 8 – Line 40 - Delete "SE" and insert - - 5E - -, therefor.

Column 10 – Line 5 - Delete "semirigid" and insert - - semi-rigid - -, therefor.

Column 10 – Line 59 - Delete "shown'" and insert - - shown - -, therefor.

Column 11 – Line 25 - Delete "plasticly" and insert - - plastically - -, therefor.

Column 13 – Line 64 - After "are" delete "Is".

Column 16 – Line 48 (Approx.) - In Claim 27, after "member" insert - - , - -.

Signed and Sealed this

Fifteenth Day of August, 2006

JON W. DUDAS  
*Director of the United States Patent and Trademark Office*